United States Patent
Onoki et al.

(10) Patent No.: US 9,829,498 B2
(45) Date of Patent: Nov. 28, 2017

(54) SAMPLING DEVICE

(71) Applicant: SHIMADZU CORPORATION, Kyoto-shi, Kyoto (JP)

(72) Inventors: Takanori Onoki, Kyoto (JP); Akiko Bamba, Kyoto (JP); Hiroyuki Otsuki, Kyoto (JP); Shoji Ide, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 157 days.

(21) Appl. No.: 14/693,228

(22) Filed: Apr. 22, 2015

(65) Prior Publication Data

US 2016/0313361 A1 Oct. 27, 2016

(51) Int. Cl.
*G01N 35/10* (2006.01)

(52) U.S. Cl.
CPC ..... *G01N 35/1004* (2013.01); *G01N 35/1011* (2013.01); *G01N 35/1079* (2013.01)

(58) Field of Classification Search
CPC ........ B08B 3/04; B08B 3/02; G01N 35/1004; G01N 35/1079; G01N 2035/1006; G01N 2035/0403; Y10T 436/11332
See application file for complete search history.

(56) References Cited

U.S. PATENT DOCUMENTS

| | | | | |
|---|---|---|---|---|
| 3,964,526 A * | 6/1976 | Sindermann | ............ | B67C 3/002 134/152 |
| 4,318,885 A * | 3/1982 | Suzuki | .................. | G01N 27/28 134/22.12 |
| 4,951,512 A * | 8/1990 | Mazza | ............... | G01N 35/1079 141/130 |
| 5,827,744 A * | 10/1998 | Fose | ......................... | B08B 3/04 134/170 |
| 6,422,248 B1 * | 7/2002 | Furst | ......................... | B08B 3/02 134/170 |
| 6,575,181 B1 * | 6/2003 | Wimmer | ................... | B08B 3/04 134/166 R |
| 7,186,378 B2 * | 3/2007 | Dunfee | .............. | G01N 35/1004 422/547 |
| 8,758,702 B2 | 6/2014 | Blouin et al. | | |

(Continued)

FOREIGN PATENT DOCUMENTS

JP    3-501168 A    3/1991
JP    2005-127896 A    5/2005

(Continued)

*Primary Examiner* — David A Rogers
(74) *Attorney, Agent, or Firm* — Sughrue Mion, PLLC

(57) ABSTRACT

A piercer washing port is provided at a position on the trajectory of a piercer differing from the sampling position. The piercer washing port is cylindrically shaped and has an opening for inserting the piercer in the upper surface and a washing space for housing the piercer inserted from the opening. Air injection ports for injecting air and washing liquid expelling ports for expelling water serving as a washing liquid are provided on the inside wall surface of the piercer washing port. The air injection ports are provided at four locations equally spaced on the periphery along the inside wall surface of the washing space. The washing liquid expelling ports 44 are provided at four locations equally spaced on the periphery along the inside wall surface of the washing space at different positions than those of the air injection ports.

12 Claims, 7 Drawing Sheets

(56) References Cited

U.S. PATENT DOCUMENTS

| | | | | |
|---|---|---|---|---|
| 9,308,560 B2* | 4/2016 | Ravalico | ............ | G01N 35/1004 |
| 2004/0175833 A1* | 9/2004 | Tatsumi | ............ | G01N 35/1097 |
| | | | | 436/49 |
| 2005/0223822 A1* | 10/2005 | Ozbal | ................ | G01N 35/1079 |
| | | | | 73/864.41 |
| 2006/0216208 A1* | 9/2006 | Li | ...................... | G01N 35/1079 |
| | | | | 422/561 |
| 2007/0065945 A1* | 3/2007 | sIGRIST | ............ | G01N 35/1011 |
| | | | | 436/43 |
| 2010/0258487 A1* | 10/2010 | Zelechonok | ........... | G01N 30/40 |
| | | | | 210/108 |
| 2013/0019699 A1* | 1/2013 | Usowicz | ................ | G01N 30/18 |
| | | | | 73/864.85 |
| 2014/0224430 A1* | 8/2014 | Yamazaki | ................ | B01D 1/14 |
| | | | | 159/4.01 |
| 2015/0314341 A1* | 11/2015 | Safavi | .................. | B01L 3/0275 |
| | | | | 134/1 |

FOREIGN PATENT DOCUMENTS

| | | |
|---|---|---|
| JP | 2005172447 A | 6/2005 |
| JP | 2008-542689 A | 11/2008 |
| JP | 2008542689 A | 11/2008 |
| JP | 5179350 B2 | 4/2013 |
| WO | 2011062982 A1 | 5/2011 |

* cited by examiner

US 9,829,498 B2

SAMPLING DEVICE

TECHNICAL FIELD

The present invention relates to a sampling device which automatically performs an operation of aspirating a sample housed in a test container using a probe and dispensing the sample at a prescribed position.

BACKGROUND ART

An automatic analyzer for automatically executing the analysis of a sample is provided with a sampling device for collecting a sample with a probe. A sampling device is a device for automatically executing an operation in which, when an analyzer installs a sample container containing a sample such as blood in a prescribed location, the sample container is transported to a prescribed aspiration position, and a probe for sample aspiration aspirates the sample in the sample container at the aspiration position and dispenses the sample at a dispensing position provided at another location.

In order to prevent the drying of the sample housed in the sample container, the upper surface of the sample container installed in the sampling machine is typically sealed by a cap consisting of an elastic member or the like. Therefore, a conventional, typical sampling machine was configured so that, when aspirating a sample in the sample container with a probe, the probe is lowered from above the sample container and is made to penetrate through the cap on the upper surface so that the tip of the probe is inserted into the sample container. However, the shavings of the cap generated when the cap is penetrated by the probe sometimes clogged the aspiration/expelling port of the probe tip.

In order to prevent the clogging of the aspiration/expelling port of the probe by the shavings of the cap, the aspiration/expelling port may be provided on the side surface of the tip part of the probe, but this makes it impossible to aspirate the entire sample housed in the sample container with the probe, which leads to the problem that the dead volume of the sample becomes large. In addition, when the aspiration/expelling port is provided on the side surface of the tip part of the probe, the drainage becomes poor, which leads to the problem that the minimum dispensing amount becomes large.

Therefore, the idea of providing the device with a piercer for penetrating and piercing the cap of the sample container separate from the probe for aspirating/expelling the sample has been proposed and implemented (see Patent Document 1). A typical piercer is a member having a cylindrical shape with a pointed tip. The piercer is lowered from above the cap so as to penetrate the cap and form a hole of a size that allows the probe to pass into the penetrated region.

In a sampling device equipped with a piercer, when a sample container to be sampled is placed at a prescribed sampling position, the piercer is first lowered from above the sample container and stopped after penetrating the cap sealing the supper surface of the sample container. A probe is then lowered from above the piercer penetrating the cap and so as to enter the sample container through a hole formed in the cap through the inside of the cylindrical piercer, and the sample in the sample container is aspirated from the tip of the probe.

When blood is collected using a vacuum blood collection tube as a sample container, a small amount of blood may remain on the cap after the probe aspirating the blood is pulled out of the cap of the blood collection tube. When a perforation operation is performed on the blood collection tube with a piercer, blood adheres to the piercer. In addition, when perforation is once again performed on a blood collection tube that has been perforated once before due to a reexamination or the like, blood as well as fine shavings of the rubber cap adhere to and contaminate the inside surface or outside surface of the piercer. In order to prevent contamination between samples due to such contamination of the piercer, it is preferable to be able to wash the piercer.

PRIOR ART DOCUMENTS

Patent Documents

[Patent document 1] Tokuhyo H3-501168
[Patent document 2] Tokuhyo 2008-542689
[Patent document 3] Japanese Unexamined Patent Application Publication 2005-127869

SUMMARY OF THE INVENTION

Problems to be Solved by the Invention

A method for washing the outside surface of a piercer is disclosed in Patent Document 2. The method disclosed in Patent Document 2 is a method of providing the device with a mechanism for spraying a washing liquid and using the mechanism to spray a washing liquid in the form of a spray over the outer peripheral surface of the piercer. However, in this method, it is necessary to spray a large amount of the washing liquid over the piercer in order to completely remove the contamination on the outside surface of the piercer, and the amount of washing liquid expended is therefore large, which leads to the problem that the container in which the used washing liquid is accumulated quickly becomes full.

In addition, in Patent Document 3 is disclosed a method of forming the space inside the piercer into a sealed space so that the washing liquid can be fed from one end side to the other end side of the piercer, and the washing liquid is fed through the space inside the piercer in a state in which the probe is inserted inside the piercer so as to simultaneously wash the inside surface of the piercer and the outer peripheral surface of the probe. However, in this method, the mechanism for sealing the space inside the piercer must be highly sealable to ensure that there is no leakage of the washing liquid from the inside of the piercer. In addition, in order to wash the outer peripheral surface of the piercer with this method, it is necessary to use a chamber having a larger inside diameter than that of the outer shape of the piercer and to feed the washing liquid into the piercer in a state in which the piercer is housed inside the chamber. This requires high sealing properties to maintain the sealed space inside the chamber and a mechanism for generating a large suction force to aspirate the washing liquid inside such a large space, which increases the cost of the device.

Therefore, the object of the present invention is to improve the washing efficiency of a piercer for perforating a cap of a sample container.

Means for Solving the Problems

A first aspect of the sampling device of the present invention comprises: a probe disposed in a perpendicular orientation so as to aspirate and expel a liquid; a piercer serving as a cylindrical member inside which the probe can pass, the tip thereof having a pointed end shape so that a cap sealing the upper surface of a sample container inside which a sample is housed is perforated by the tip; a probe driving mechanism for driving the probe in the horizontal plane direction and in the vertical direction; a piercer driving mechanism for driving the piercer in the horizontal plane direction and in the vertical direction; a piercer washing port provided at a position to which the piercer can move, the position differing from the position at which the piercer executes the perforation operation of the cap on the upper surface of the sample container, the piercer washing port having an opening in the upper surface and a washing space for washing the piercer inserted from the opening, and a washing liquid discharge channel for discharging the washing liquid being connected beneath the washing space; a washing liquid expelling mechanism provided on the piercer washing port so as to simultaneously expel the washing liquid from a plurality of washing liquid expelling ports disposed at equal spaces on the periphery along the inside wall surface of the washing space to the piercer inserted into the washing space and to thereby form a film consisting of a washing liquid in the circumferential direction on the outer peripheral surface of the piercer; and a controller for controlling the operations of the probe driving mechanism, the piercer driving mechanism, and the washing liquid expelling mechanism, the controller being equipped with a piercer outside surface washer for executing a piercer outside surface washing operation to expel the washing liquid from the washing liquid discharge mechanism in a state in which the piercer is disposed inside the washing space.

A second aspect of the sampling device of the present invention comprises: a probe disposed in a perpendicular orientation so as to aspirate and discharge a liquid; a piercer serving as a cylindrical member inside which the probe can pass, the tip thereof having a pointed end shape so that a cap sealing the upper surface of a sample container inside which a sample is housed is perforated by the tip; a probe driving mechanism for driving the probe in the horizontal plane direction and in the vertical direction; a piercer driving mechanism provided as a separate mechanism from the probe driving mechanism so as to drive the piercer in the horizontal plane direction and in the vertical direction; a piercer washing nozzle positioned above the piercer so as to be able to expel a washing liquid into the piercer; a washing liquid discharge port for discharging the washing liquid expelled from the piercer washing nozzle; and a controller for controlling the operations of the probe driving mechanism, the piercer driving mechanism, and the piercer washing nozzle, the controller having a piercer inside surface washer for executing a piercer inside surface washing operation to expel the washing liquid from the piercer washing nozzle toward the inside of the piercer in a state in which the piercer is disposed inside the washing liquid discharge port and the piercer washing nozzle is disposed above the piercer.

Effect of the Invention

As a result of experimentally verifying differences in the washing efficiency of the outer peripheral surface of the piercer based due to the washing method, the present inventors discovered that the outer peripheral surface of the piercer can be most washed most efficiently by forming a film of the washing liquid in the circumferential direction on the outer peripheral surface of the piercer, and that a higher washing effect is achieved with a smaller amount of washing liquid than when washing by simply spraying a spray-type washing liquid onto the piercer. The first aspect of the present invention was based on this knowledge.

The first aspect of the sampling device of the present invention is equipped with a piercer washing port having a washing space for washing the piercer, and a washing liquid expelling mechanism is provided on the piercer washing port to form a film consisting of the washing liquid in the circumferential direction on the outer peripheral surface of the piercer by simultaneously expelling the washing liquid from a plurality of washing liquid expelling ports disposed at equal spaces on the periphery along the inside wall surface of the of the washing space to the piercer inserted into the washing space. The controller for controlling the operations of the probe driving mechanism, the piercer driving mechanism, and the washing liquid expelling mechanism, is provided with a piercer outside surface washer for expelling the washing liquid from the washing liquid expelling mechanism in a state in which the piercer is disposed inside the washing space. Therefore, it is possible to efficiently wash the outer peripheral surface of the piercer with a smaller amount of washing liquid than when washing by simply spraying a spray-type washing liquid onto the piercer.

In addition, in a system in which the probe is inserted into the sample container through the inside of the piercer, the sample adhering to the outer peripheral surface of the probe may adhere to the inside surface of the piercer. However, in a device in which the driving mechanism of the piercer and the probe is shared and the piercer and the probe are disposed coaxially, it is possible to wash the inside surface with the method disclosed in Patent Document 3, but this required a mechanism for sealing the space inside the piercer with high sealing properties and a mechanism for aspirating the washing liquid supplied into the piercer with a strong suction force.

According to the second aspect of the sampling device of the present invention, the piercer driving mechanism is a separate mechanism from the probe driving mechanism, and the device is provided with a piercer washing nozzle positioned above the piercer so as to be able to expel a washing liquid into the piercer, and a washing liquid discharge port for discharging the washing liquid expelled from the piercer washing nozzle. Therefore, it is possible to wash the inside surface of the piercer by expelling the washing liquid from the piercer washing nozzle toward the inside of the piercer in a state in which the piercer is disposed inside the washing liquid discharge port and the piercer washing nozzle is disposed above the piercer. Further, the controller for controlling the operations of the sampling device is equipped with a piercer inside surface washer for executing the piercer inside surface washing operation described above, so the device executes the washing of the inside surface of the piercer automatically as necessary, which prevents problems such as contamination due to the sample adhering to the inside surface of the piercer.

Figure 1:
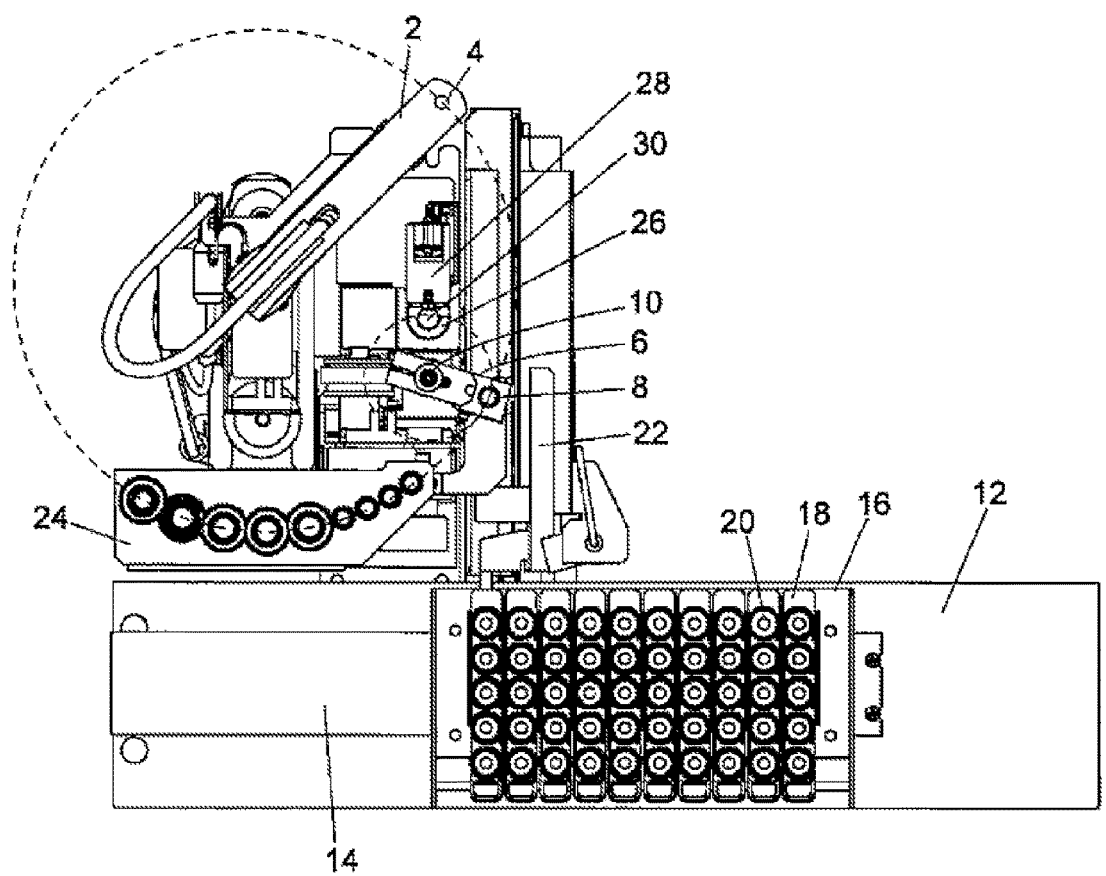
FIG. 1 is a plan view illustrating an embodiment of a sampling device.

DETAILED DESCRIPTION OF THE
EXEMPLARY EMBODIMENTS

In the first aspect of the sampling device of the present invention, the piercer outside surface washing operation is preferably performed by moving the piercer in the vertical direction while forming a film consisting of the washing liquid in the circumferential direction on the outer peripheral surface of the piercer so that the film formation range covers the washing range of the outer peripheral surface of the piercer.

When the inside wall surface of the washing space surrounding the periphery of the piercer is in close proximity to the piercer, even if a film of the washing liquid is formed by expelling the washing liquid onto the outer peripheral surface of the piercer from the periphery thereof, some of the washing liquid may move to the inside wall surface side of the washing space so that a film is not formed from an intermediate stage. Therefore, the washing of the outer peripheral surface of the piercer may be insufficient when simply expelling the washing liquid from the washing liquid expelling mechanism in a state in which the piercer is stopped at a certain position. Accordingly, it is possible to prevent the washing of the outer peripheral surface of the piercer from being insufficient by moving the piercer in the vertical direction while forming a film consisting of the washing liquid in the circumferential direction on the outer peripheral surface of the piercer so that the film formation range covers the washing range of the outer peripheral surface of the piercer.

In the first aspect of the sampling device of the present invention, the washing liquid expelling mechanism is preferably configured so as to expel the washing liquid in a diagonally downward direction from the washing liquid expelling port. As a result, it becomes easy for a film consisting of the washing liquid to be formed in the circumferential direction of the outer peripheral surface of the piercer, and the washing power of the outer peripheral surface of the piercer improves.

In the first aspect of the sampling device of the present invention, the piercer washing port is preferably further equipped with an air injection mechanism for blowing air onto the piercer housed in the washing space from the periphery thereof, and the controller is preferably further equipped with a piercer outside surface dryer for executing a piercer outside surface drying operation of blowing air onto the piercer from the air injection mechanism. This makes it possible to automatically dry the piercer after being washed inside the piercer washing port.

The air injection mechanism is preferably configured so as to blow air onto the piercer in a diagonally downward direction. This makes it possible to efficiently spray the washing liquid adhering to the outer peripheral surface of the piercer to the washing liquid discharge channel side and to improve the drying efficiency of the outer peripheral surface of the piercer.

In the second aspect of the sampling device of the present invention, the piercer washing nozzle is preferably able to inject air at a timing differing from that of the washing liquid, and the controller is preferably further equipped with a piercer inside surface dryer for executing a piercer inside surface drying operation of injecting air from the piercer washing nozzle in a state in which the piercer is disposed inside the washing liquid discharge port and the piercer washing nozzle is disposed above the piercer. This makes it possible to execute the drying of the inside surface of the piercer in this state after executing the washing of the inside surface of the piercer.

Further, in the second aspect of the sampling device of the present invention, a piercer washing port is preferably provided as a washing liquid discharge port at a position to which the piercer can move, the position differing from the position at which the piercer executes the perforation operation of the cap on the upper surface of the sample container, and the piercer washing port having an opening in the upper surface and a washing space for washing the piercer inserted from the opening. The piercer washing port is preferably provided with a washing liquid expelling mechanism for simultaneously expelling the washing liquid to the piercer inserted into the washing space from a plurality of positions around the periphery thereof. The controller is preferably further equipped with a piercer outside surface washer for executing a piercer outside surface washing operation of expelling the washing liquid from the washing liquid expelling mechanism and forming a film consisting of the washing liquid in the circumferential direction on the outer peripheral surface of the piercer in a state in which the piercer is disposed inside the washing space. This makes it possible to simultaneously wash both the inside surface and the outside surface of the piercer in a state in which the piercer is inserted into the piercer washing port, which makes it possible to further improve the washing efficiency of the piercer.

As described above, the outer peripheral surface of the piercer can be washed with the configuration disclosed in Patent Document 2, and the inside surface of the piercer can be washed with the configuration disclosed in Patent Document 3, but both the outer peripheral surface and the inside surface of the piercer cannot be washed simultaneously by utilizing either of these configurations.

In the cases described above, as in the case of the first aspect of the present invention, the piercer outside surface washing operation is preferably performed by moving the piercer in the vertical direction while forming a film consisting of the washing liquid in the circumferential direction on the outer peripheral surface of the piercer so that the film formation range covers the washing range of the outer peripheral surface of the piercer.

In addition, the piercer washing port is preferably further equipped with an air injection mechanism for blowing air onto the piercer housed in the washing space from the periphery thereof, and the controller is preferably further equipped with a piercer outside surface dryer for executing a piercer outside surface drying operation of blowing air onto the piercer from the air injection mechanism in a state in which the piercer is disposed inside the washing liquid discharge port and the piercer washing nozzle is disposed above the piercer. This makes it possible to automatically dry the piercer after being washed inside the piercer washing port.

The air injection mechanism is preferably configured so as to blow air onto the piercer in a diagonally downward direction. This makes it possible to efficiently spray the washing liquid adhering to the outer peripheral surface of the piercer to the washing liquid discharge channel side and to improve the drying efficiency of the outer peripheral surface of the piercer.

Further, the device is preferably further equipped with a washing sequence holding part for holding the timing at which each of the operations including the piercer inside surface washing operation, the piercer outside surface washing operation, the piercer inside surface drying operation, and the piercer outside surface drying operation when the washing of the piercer is executed. The washing sequence holding part preferably holds a washing sequence configured so that the piercer inside surface drying operation is executed after executing the piercer inside surface washing operation and the piercer outside surface washing operation and so that the piercer outside surface drying operation is executed during the execution of the piercer inside surface drying operation. When air is first injected downward toward the inside of the piercer from the piercer washing nozzle, the washing liquid adhering to the inside surface of the piercer drops down below the piercer. When the washing liquid on the inside surface of the piercer drops down, a negative pressure is generated by the Venturi effect beneath the piercer, and when air is blown toward the outer peripheral surface of the piercer from the periphery of the piercer at this timing, the washing liquid or air around the piercer assumes a negative pressure and is aspirated downward from the piercer. This makes it possible to efficiently dry the outer peripheral surface of the piercer while preventing the scattering of the washing liquid to the periphery of the piercer.

An embodiment of the sampling device of the present invention will be described hereinafter with reference to the drawings. First, the overall configuration of the sampling device will be described using FIG. 1. FIG. 1 is a plan view from above, so the in-plane direction of the page is the horizontal direction, and the direction perpendicular to the page is the vertical direction.

A probe 4 for aspirating and expelling a sample is mounted on the tip part of a probe arm 2 serving as a probe driving mechanism with the tip facing downward. By driving the rotation of the probe 4 in the horizontal plane, the probe arm 2 can move the probe 4 in the horizontal plane direction and in the vertical direction. A position on the trajectory of the probe 4 and on the trajectory of a piercer 8 described below (illustrated position) is set as a sampling position. The sampling position is a position at which a perforation operation is performed by the piercer 8 on a cap of a sample container and at which the sample is collected by the probe 4.

A piercer arm 6 extending in the horizontal direction with a height lower than that of the probe arm 2 is provided at a position differing from that of the probe arm 2. The piercer arm 6 is driven to rotate within the horizontal plane around a driving shaft 10 on the base end side. A piercer 8 is held on the tip part of the piercer arm 6 in a state in which the tip part thereof faces downward. The piercer 8 is a cylindrical member having an inside diameter larger than the outside diameter of the probe 4, and the tip part has a pointed shape.

The piercer 8 is driven by the piercer arm 6 serving as a piercer driving mechanism so as to draw an arc in the horizontal plane direction and can move in the vertical direction. The trajectory of the piercer 8 in the horizontal plane direction is set so as to pass through the sampling position set on the trajectory of the probe 4 in the horizontal plane direction. A cap on the upper surface of a sample container carried to the sampling position is penetrated and perforated by the piercer 8, and the probe 4 can then be lowered from above the piercer 8 penetrating the cap and passed into the piercer 4 so as to insert the probe 4 into the sample container.

Sample containers 20 housing samples to be collected by the probe 4 are held in a row by a sample rack 18 for a certain number of containers (five containers in this embodiment), and the sample racks 18 are installed in a sample tray 16. The sample tray 16 is disposed on a belt 14 of a conveyor 12 so as to be transported in one direction. A handler 22 is provided to hold the sample racks 18 installed in the sample tray 16 and to extract the sample racks 18 in a direction perpendicular to the transporting direction of the conveyor 12. The handler 22 can hold a sample rack 18 transported to a prescribed position by the conveyor 12 and can move a given sample container 20 out of the sample containers 20 held in that sample rack 18 to the sampling position.

A piercer washing port 26 is provided at a position on the trajectory of the piercer 8 differing from the sampling position. A water pouring arm 28 which holds a piercer washing nozzle 30 with the tip end part thereof is provided. The water pouring arm 28 holds the piercer washing nozzle 30 at a position higher than the upper end of the piercer 8 (front side in the direction perpendicular to the page) so that the nozzle opening faces downward, and the arm can place the piercer washing nozzle 30 at a position on the piercer washing port 26. The piercer washing port 26 and the piercer washing nozzle 30 will be described below.

This sampling device is provided with a specimen installation part 24 for installing sample containers to be sampled separately from the sample containers 20 installed in the sample tray 16. With the specimen installation part 24, sample containers in a state with the upper surface opened are disposed at a position on the trajectory of the probe 4. When the sampling of these sample containers is executed, the probe 4 moves to the position of a sample container installed in the specimen installation part 24, and sampling is then performed.

Figure 6:
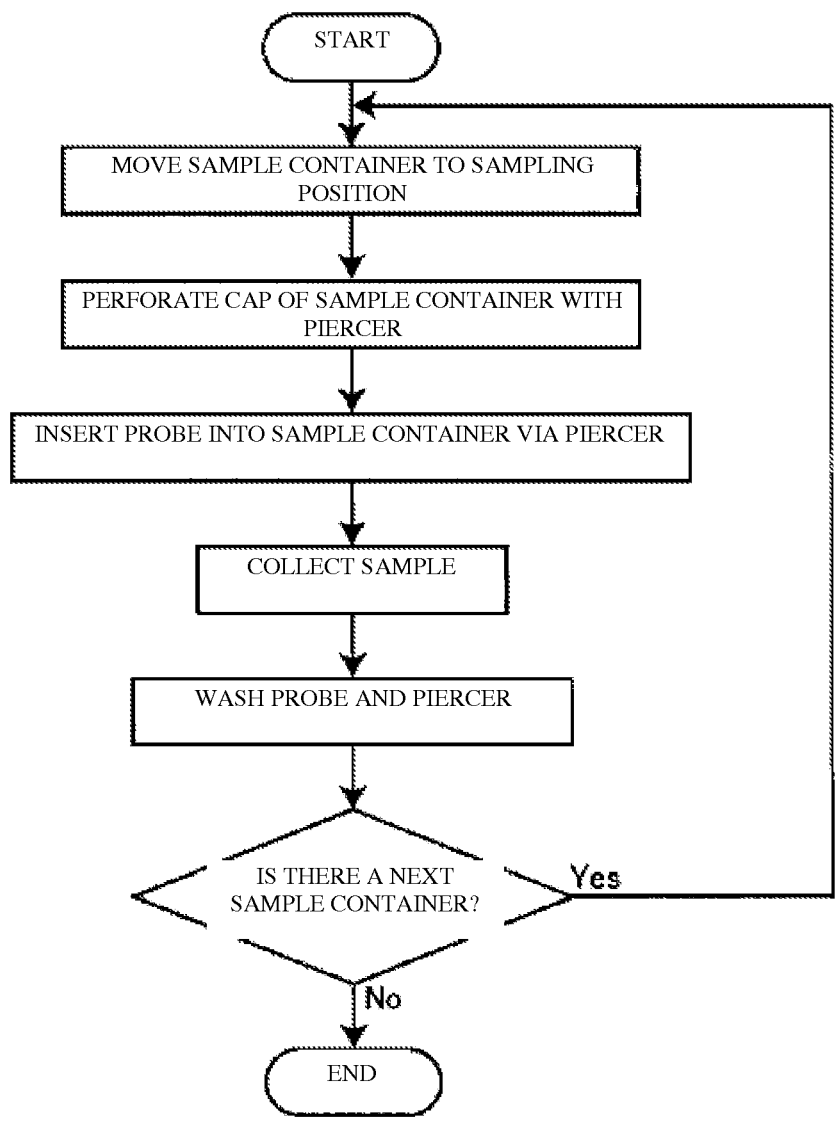
FIG. 6 is a flowchart for explaining the sampling operation of this embodiment.

An example of the sampling operation of this sampling device will be described using FIG. 6.

First, a sampling container 20 to be sampled is transported to a prescribed sampling position by the conveyor 12 and the handler 22. The piercer is placed at a position above the sample container 20 transported to the sampling position and is lowered from that position. The cap of the sample container 20 is penetrated by the tip of the piercer 8 so as to perforate the cap. By placing the probe 4 at a position above the piercer 8 and lowering the probe from that position, the probe 4 is inserted into the sample container 20 via the piercer 8, and the sample is aspirated and collected from the tip of the probe 4.

The probe 4 that collected the sample is pulled out of the sample container 20 and moved to the position of an analyzer (not illustrated) provided at another position, and the sample is then dispensed into the analyzer. The probe 4 and the piercer 8 are then respectively moved to prescribed washing ports and washed. The washing of the piercer 8 is performed at the piercer washing port 26. The washing of the piercer 8 will be described in detail below. Next, if there is a sample container to be sampled, the operation described above is repeatedly executed for the next sample container.

Figure 4:
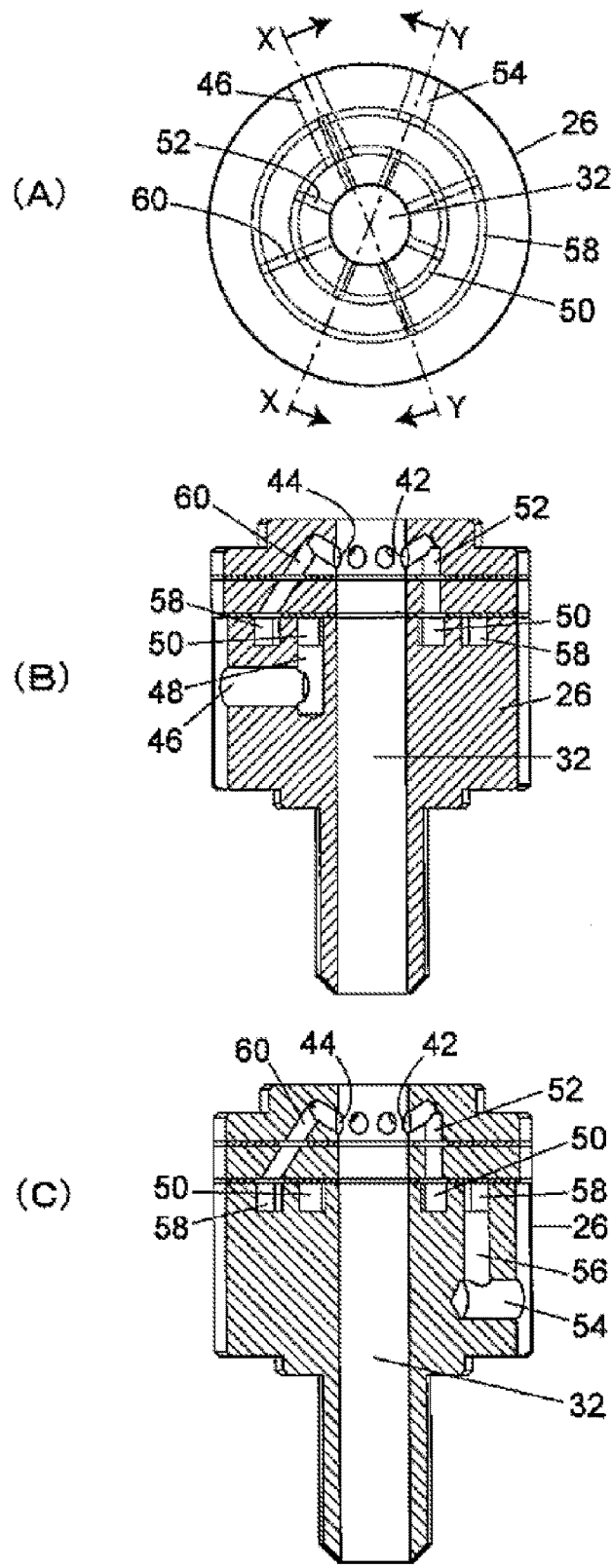
FIG. 4 illustrates the structure of a piercer washing port in this embodiment, wherein (A) is a plan view, (B) is a cross-sectional view along the X-X position in (A), and (C) is a cross-sectional view along the Y-Y position in (A).

The piercer washing mechanism consisting of the piercer washing port 26 and the piercer washing nozzle 30 will be described hereinafter. First, the structure of the piercer washing port 26 will be described using FIG. 4.

The piercer washing port 26 is cylindrically shaped and has an opening for inserting the piercer 8 in the upper surface and a washing space 32 for housing the piercer 8 inserted from the opening. A tube 34 (see FIGS. 2 and 3) serving as a washing liquid discharge channel is connected to the lower part of the piercer washing port 26, and a washing space 32 communicates with the tube 34. The washing space 32 serves as a channel having a uniform inside diameter from the upper end to the lower end, and the inside diameter thereof is slightly larger than the outer shape of the piercer 8. For example, when the outside diameter of the piercer 8 is approximately 4 mm, the inside diameter of the washing space 32 is approximately 8 mm.

Air injection ports 42 for injecting air and washing liquid expelling ports 44 for expelling water serving as a washing liquid are provided on the inside wall surface of the piercer washing port 26. The air injection ports 42 are provided at four locations equally spaced on the periphery along the inside wall surface of the washing space 32. The washing liquid expelling ports 44 are provided at four locations equally spaced on the periphery along the inside wall surface of the washing space 32 at different positions than those of the air injection ports 42. The air injection ports 42 and the washing liquid expelling ports 44 are arranged with equal spacing on the same periphery of the inside wall surface of the washing space 32.

The piercer washing port 26 is equipped with two circular channels 50 and 58 as internal channels forming circles in the horizontal plane. The circular channel 50 is formed inside the circular channel 58 within the same plane as the circular channel 58. The air injection ports 42 communicate with the circular channel 50 via a channel 52, and the washing liquid expelling ports 44 communicate with the circular channel 58 via a channel 60.

An air supply port 46 into which an air supply tube is inserted so as to connect to an internal channel and a washing liquid supply port 54 into which a washing liquid supply tube is inserted so as to connect to an internal channel are provided on the outside surface of the piercer washing port 26. The air supply port 46 communicates with a channel 48 connected to the circular channel 50, and the washing liquid supply port 54 communicates with a channel 56 connected to the circular channel 58. With this structure, when air is supplied from the air supply tube connected to the air supply port 46, the air is injected from the air injection ports 42 at four locations through the channel 48, the circular channel 50, and the channel 52. Similarly, when water is supplied from the washing liquid supply tube connected to the washing liquid supply port 54, the water is expelled from the washing liquid expelling ports 44 at four locations through the channel 56, the circular channel 58, and the channel 60.

In this embodiment, the inside diameter of the washing space 32 is uniform from the upper end to the lower end, but the shape of the washing space 32 is not limited to this configuration and may be configured so that the cross-sectional area gradually increases toward the bottom on the lower side of the air injection ports 42 or so that the cross-sectional area of the portion below the tip of the piercer 8 inserted into the washing space 32 is greater than the cross-sectional area of the portion above the tip.

Figure 2:
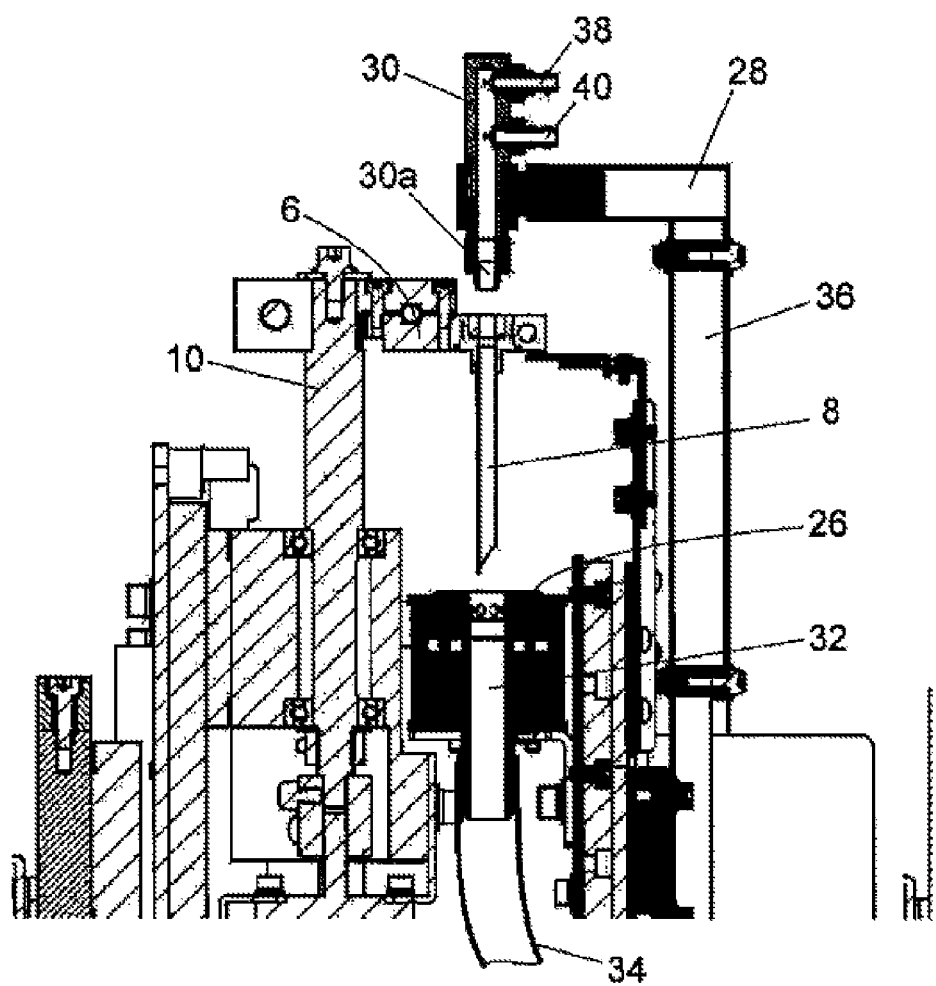
FIG. 2 is cross-sectional side view illustrating a state prior to the piercer washing operation of the piercer washing mechanism in this embodiment.

The washing of the piercer 8 is executed in the washing space 32 inside the piercer washing port 26 described above. When the washing of the piercer 8 is executed, as illustrated in FIG. 2, the piercer 8 is disposed at a position on the piercer washing port 26, and the piercer washing nozzle 30 is disposed above the piercer. The piercer washing nozzle 30 is driven in the vertical direction as a nozzle driving shaft 36 supporting the base end of the water pouring arm 28 moves vertically, and the tip part 30a of the piercer washing nozzle 30 is thereby attached to or detached from the upper end part of the piercer 8. An air supply tube 38 and a washing liquid supply tube 40 are connected to the base end side of the piercer washing nozzle 30 so that either air or the washing liquid can be expelled diagonally downward from the tip 30a of the piercer washing nozzle 30.

The inside diameter of the piercer washing nozzle 30 is greater than the inside diameter of the piercer 8. By expelling the washing liquid in a state in which the tip 30a of the piercer washing nozzle 30 is in close contact with the upper end of the piercer 8, it is possible to wash contamination adhering to the inside surface of the piercer 8 downward with the washing liquid. In addition, when the tip 30a of the piercer washing nozzle 30 is brought into close contact with the upper end of the piercer 8, a seal is formed on the channel inside the piercer washing nozzle 30 and on the channel inside the piercer 8 so that the washing liquid or air does not leak to the outside from the piercer washing nozzle 30.

Figure 3:
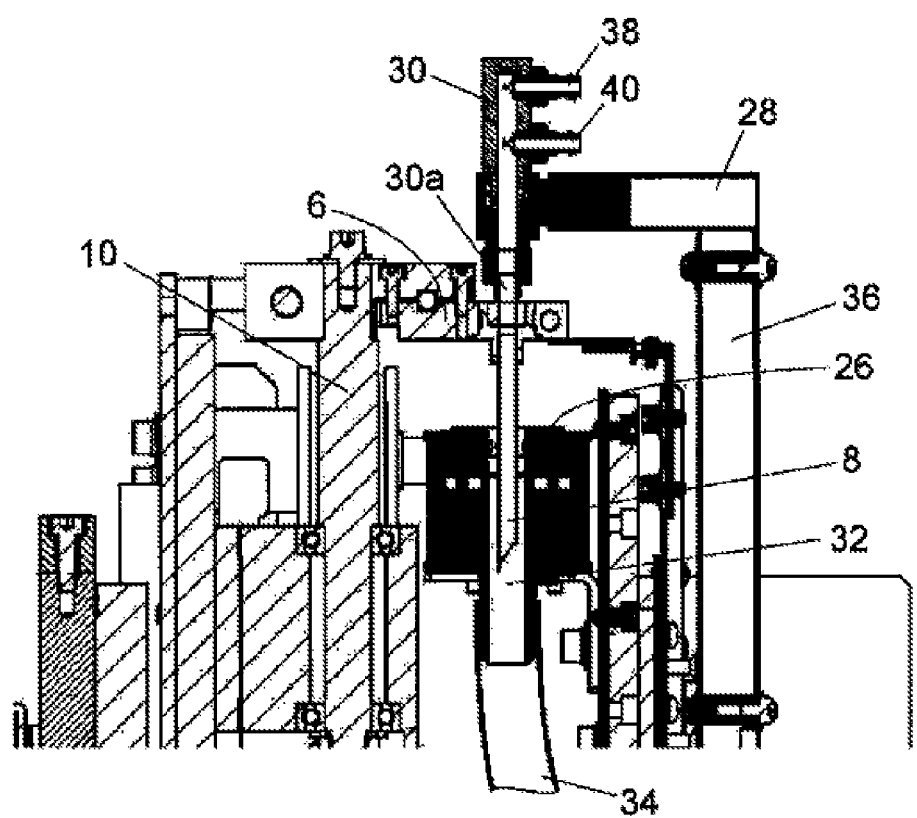
FIG. 3 is cross-sectional side view illustrating a state at the time of the piercer washing operation of the piercer washing mechanism in this embodiment.

The piercer washing port 26 is for washing the outer peripheral surface of the piercer 8, and the piercer washing nozzle 30 is for washing the inside surface of the piercer 8, but the piercer washing port 26 also fulfills the roll of a washing liquid discharge port for discharging the washing liquid expelled from the piercer washing nozzle 30. As illustrated in FIG. 3, when the piercer 8 is inserted into the washing space 32 of the piercer washing port 26 and water serving as a washing liquid is sprayed onto the piercer 8 from the washing liquid expelling ports 44 on the inside wall surface of the washing space 32, the outer peripheral surface of the piercer 8 is washed, and the water sprayed onto the piercer 8 is discharged from the tube 34. In addition, when the tip 30a of the piercer washing nozzle 30 is brought into close contact with the upper end of the piercer 8 and water serving as a washing liquid is expelled in a state in which the piercer 8 is inserted into the washing space 32, the inside surface of the piercer 8 is washed, and the water passing through the inside of the piercer 8 is discharged from the tube 34.

Here, the tube 34 for discharging the washing liquid has a sufficiently large inside diameter (for example, 8 to 12 mm) with respect to the shavings (for example, an outside diameter of approximately 0.1 to 2 mm) of the cap of the sample container washed away by the washing of the inside surface or the outer peripheral surface of the piercer 8. A filter or the like for collecting the shavings of the cap washed away by washing is not provided at the end on the washing space 32 side of the tube 34, and the shavings of the cap washed away by washing are accumulated in a prescribed waste liquid tank through the tube 34 together with the washing liquid. As a result, clogging does not occur in the tube 34 due to the shavings of the cap, and the problem of reduced washing efficiency or drying efficiency over time does not occur.

Here, the channel 52 has a shape such that air is injected diagonally downward from the air injection ports 42 and so that the air from the circular channel 50 is guided to the air injection ports 42 from positions higher than the air injection ports 42. This makes it possible to improve the drying efficiency of the outer peripheral surface of the piercer 8 by air injected from the air injection ports 42. The angle formed by the air injected from the air injection ports 42 and the inside wall surface of the washing space 32 is 60°, for example.

Similarly, the channel 60 has a shape such that the washing liquid is expelled diagonally downward from the washing liquid expelling ports 44 and so that the washing liquid from the circular channel 58 is guided to the washing liquid expelling ports 44 from positions higher than the washing liquid expelling ports 44. As a result, it becomes easy for a film of the washing liquid to be formed on the outer peripheral surface of the piercer 8, and the washing efficiency of the outer peripheral surface of the piercer 8 improves. The angle formed by the washing liquid expelled from the washing liquid expelling ports 44 and the inside wall surface of the washing space 32 is 60°, for example.

Figure 5:
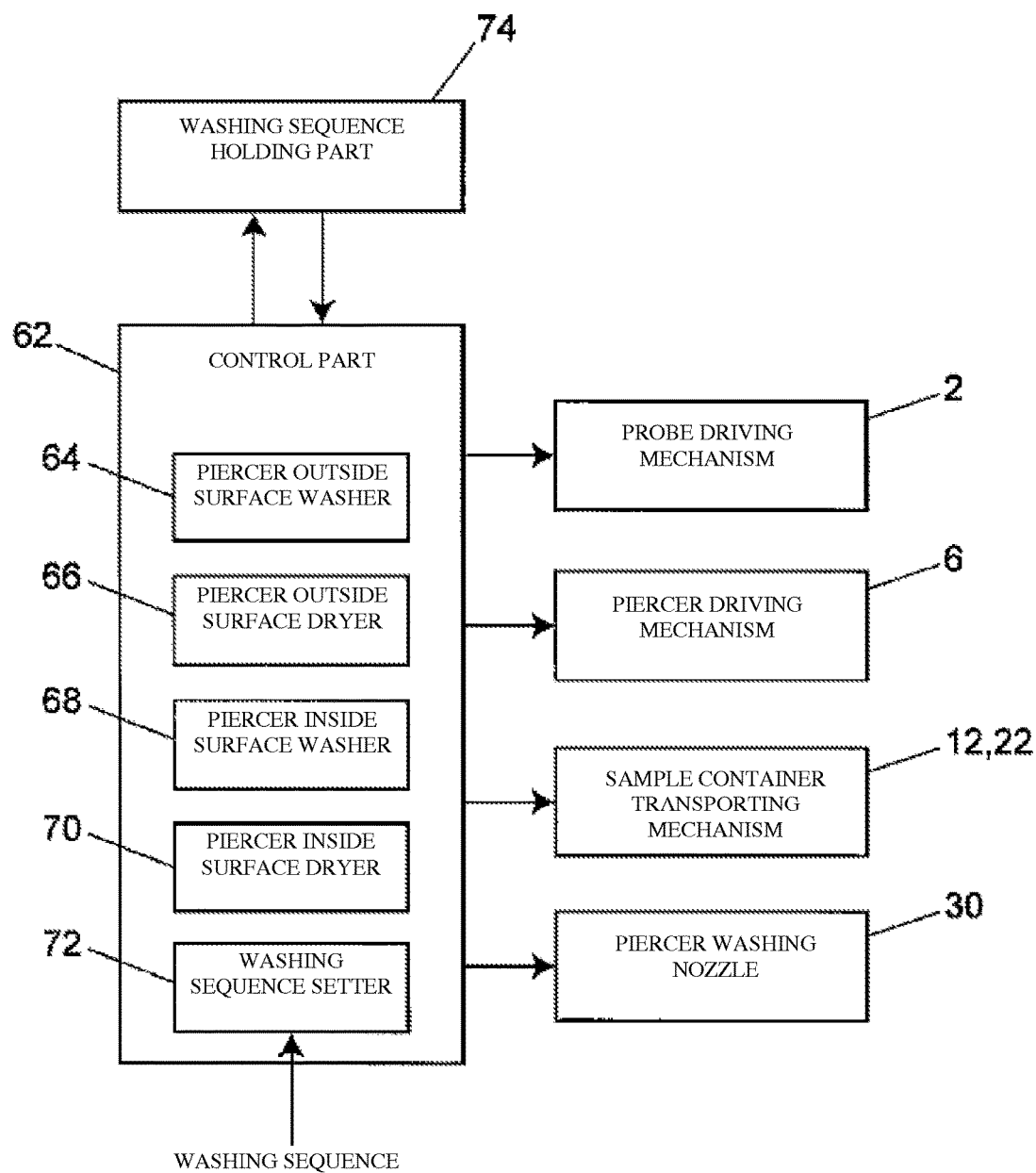
FIG. 5 is a block diagram schematically illustrating the control system of this embodiment.

The control system of this embodiment will be described using FIG. 5.

The operations of the sampling device are controlled by a controller 62. The controller 62 controls the operations of the probe driving mechanism (probe arm) 2, the piercer driving mechanism (piercer arm) 6, the sample transporting mechanism such as the conveyor 12 or the handler 22, and the piercer washing nozzle 30 (including the water pouring arm 28) and executes various operations.

In order to execute the washing of the piercer 8, the controller 62 is equipped with a piercer outside surface washer 64, a piercer outside surface dryer 66, a piercer inside surface washer 68, a piercer inside surface dryer 70, and a washing sequence setter 72. The piercer outside surface washer 64 is configured to execute a piercer outside surface washing operation of washing the outer peripheral surface of the piercer 8, and the piercer outside surface dryer 66 is configured to execute a piercer outside surface drying operation of drying the outside surface of the piercer 8 after washing. In addition, the piercer inside surface washer 68 is configured to execute a piercer inside surface washing operation of washing the inside surface of the piercer 8, and the piercer inside surface dryer 70 is configured to execute a piercer inside surface drying operation of drying the inside surface of the piercer 8 after washing.

The washing sequence setter 72 is to be used by the operator of the sampling device to set the order of the respective operations of the washing of the piercer 8 as desired, and the set washing sequence is held in a washing sequence holding part 74. In addition to washing sequences set by the operator, predetermined washing sequences are held in the washing sequence holding part 74. In accordance with a washing sequence held in the washing sequence holding part 74, the controller 62 controls the operations of the probe driving mechanism 2, the piercer driving mechanism 6, the sample transporting mechanisms 12 and 22, and the piercer washing nozzle 30 so that the respective operations are performed in the order of the sequence.

The controller 62 is realized by a dedicated computer provided in the sampling device or a general-purpose personal computer connected to the sampling device. The washing sequence holding part 74 is illustrated as a separate unit from the controller 62, but it is actually realized by a storage device provided in the dedicated computer or a storage device provided in the general-purpose personal computer constituting the controller 62.

The piercer outside surface washing operation described above is an operation of inserting the piercer 8 into the washing space 32 and slowly lowering or raising the piercer 8 while forming a film of water in the circumferential direction of the outer peripheral surface of the piercer 8 by uniformly expelling water from the washing liquid expelling ports 44 at four locations provided on the inside wall surface of the washing space 32. By forming a film of water in the circumferential direction of the outer peripheral surface of the piercer 8, it is possible to eliminate washing irregularities with a smaller amount of water than when simply spraying water toward the piercer 8. When the surrounding wall surface is close to the piercer 8, the water traveling along the outer peripheral surface of the piercer 8 moves to the wall surface side around the piercer 8 so that the film is no longer formed from an intermediate stage, so the range over which the film of water is formed in the circumferential direction of the outer peripheral surface of the piercer 8 is limited to a part of the vicinity of the portion sprayed with water. Therefore, the washing of the piercer 8 covers the necessary portions as a result of lowering or raising the piercer 8 while uniformly spraying water from the washing liquid expelling ports 44 so that the entire required range of the outer peripheral surface of the piercer 8 is washed.

The piercer outside surface drying operation is an operation of blowing the water on the outer peripheral surface of the piercer 8 downward by blowing air diagonally downward toward the piercer 8 from the air injection ports 42 in a state in which the piercer 8 is inserted into the washing space 32 after the piercer outside surface washing operation. This operation is executed in a state in which the piercer 8 is inserted into the washing space 32 so that the uppermost part of the washed portion of the outer peripheral surface of the piercer 8 is located at the position where air is blown or at a position lower than this position. In addition, the piercer 8 does not necessarily have to be stopped during the piercer outside surface drying operation, and the piercer 8 may also be raised slowly while air is blown onto the piercer.

The piercer inside surface washing operation is an operation of inserting the piercer 8 into the piercer washing port 26 and expelling water serving as a washing liquid from the piercer washing nozzle 30 in a state in which the tip 30*a* of the piercer washing nozzle 30 is brought into close contact with the upper end of the piercer 8. The piercer inside surface drying operation is an operation of drying the surface by blowing water adhering to the inside surface of the piercer 8 downward by injecting air from the piercer washing nozzle 30 after the completion of the piercer inside surface washing operation.

Figure 7:
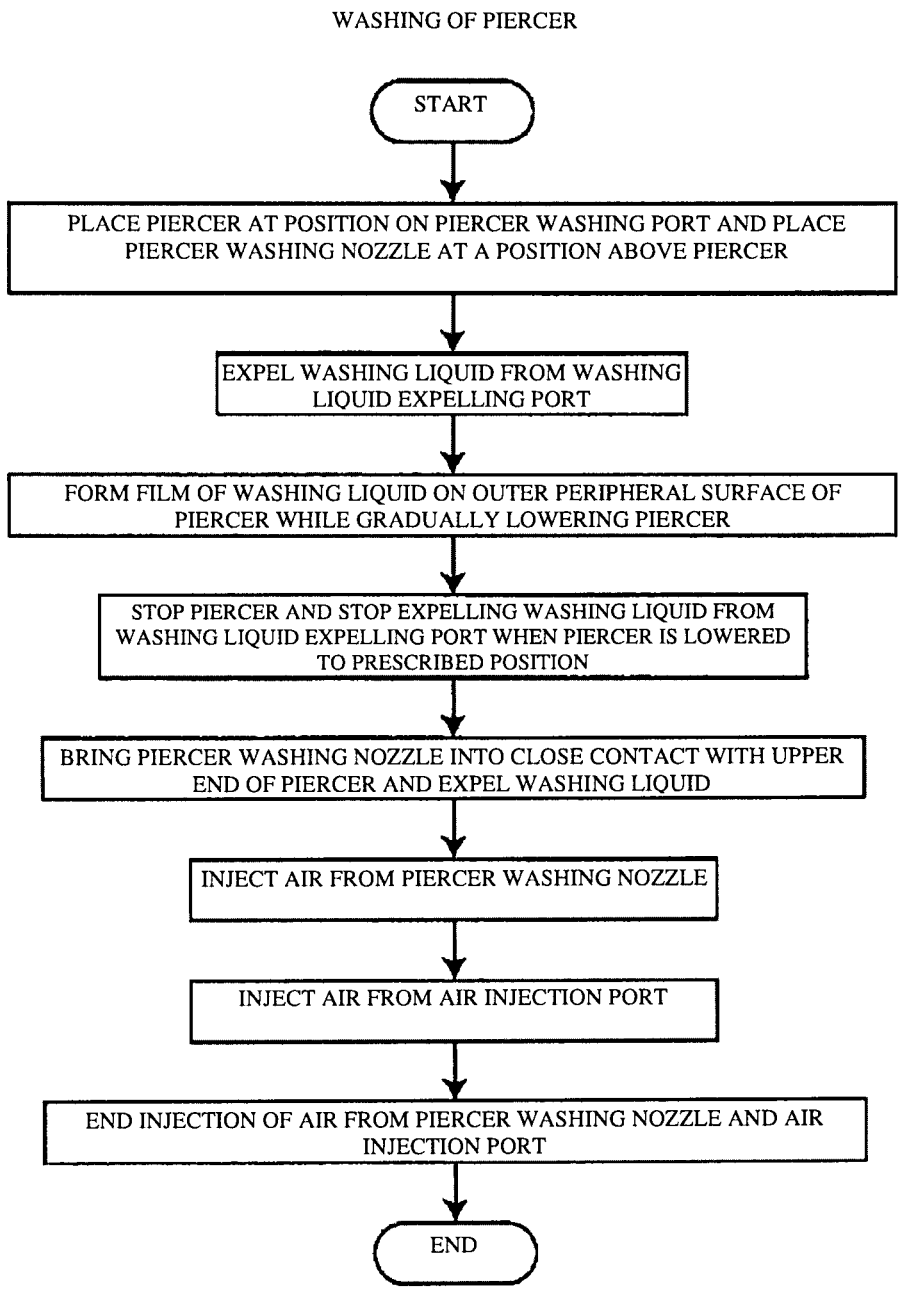
FIG. 7 is a flowchart for explaining the piercer washing operation of this embodiment.

A preferable example of a washing sequence of the piercer 8 will be described using FIG. 7.

As illustrated in FIG. 3, the piercer 8 is disposed at a position on the piercer washing port 26, and the piercer washing nozzle 30 is disposed at a position above the piercer 8. Water is expelled from the washing liquid expelling ports 44 of the piercer washing port 26, and the piercer 8 is inserted into the washing space 32 of the piercer washing port 26 and lowered. At this time, a film of water serving as a washing liquid is formed on the outer peripheral surface of the piercer 8.

Once the piercer 8 has been lowered to a prescribed position at which all of the locations of the outer peripheral surface of the piercer 8 that need to be washed have been washed, the piercer 8 is stopped, and the expelling of water from the washing liquid expelling ports 44 is terminated. Next, the inside surface of the piercer 8 is washed by lowering the piercer washing nozzle 30, bringing the tip 30*a* thereof into close contact with the upper end of the piercer 8, and expelling water serving as a washing liquid from the piercer washing nozzle 30. After the washing of the inside surface of the piercer 8 is complete, air is injected from the piercer washing nozzle 30 after a certain amount of time (for example, 0.4 seconds) has passed after air is first injected from the piercer washing nozzle 30, and air is injected toward the outer peripheral surface of the piercer 8 from the air injection ports 42 in this state for a certain amount of time (for example, 0.05 seconds).

In the washing sequence described above, either the washing of the outer peripheral surface of the piercer 8 or the washing of the inside surface of the piercer 8 may be executed first, or they may be executed simultaneously. When air is injected in a perpendicular direction from the tip of the piercer 8, air is injected from the tip of the piercer 8 to the piercer washing port 26 having a larger inside diameter than the piercer 8 at a position beneath the piercer 8, which results in the Venturi effect and generates a region of negative pressure beneath the piercer 8. When air is blown toward the outer peripheral surface of the piercer 8 from the periphery of the piercer 8 at this timing, the washing liquid or air around the piercer 8 is aspirated to beneath the piercer where a negative pressure is formed. This makes it possible to efficiently dry the outer peripheral surface of the piercer 8 while preventing the scattering of the washing liquid to the periphery of the piercer 8.

In addition, when a liquid is mixed with the air injected from the tip of the piercer 8, the Venturi effect becomes greater. By using this to blow air from the periphery of the piercer 8 toward the outer peripheral surface of the piercer 8 at a timing immediately after the washing liquid adhering to the inside surface of the piercer 8 drops down to beneath the piercer 8, it is possible to further enhance the drying effect of the outer peripheral surface of the piercer 8 and the effect of preventing the scattering of the washing liquid.

With this washing sequence, although also dependent on the amount of flow of the washing liquid or the amount of flow of air blown onto the piercer, a rapid washing operation may be performed in which, for example, the outer peripheral surface and the inside surface of the piercer 8 are washed simultaneously for approximately 0.5 seconds, and the outer peripheral surface and the inside surface of the piercer 8 are then dried for approximately 0.5 seconds after a standby period of approximately 0.5 seconds.

EXPLANATIONS OF SYMBOLS 2 probe arm
4 probe
6 piercer arm
8 piercer
10 piercer driving shaft
12 conveyor
14 conveyor belt
16 sample tray
18 sample rack
20 sample container
22 handler
24 specimen installation part
26 piercer washing port
28 water pouring arm
30 piercer washing nozzle
32 washing space of the piercer washing port
34 tube (washing liquid discharge channel)
36 water pouring arm driving shaft
38 air supply tube
40 washing liquid supply tube
42 air injection port
44 washing liquid expelling port
46 air supply port
48, 50, 52, 56, 58, 60 internal channels of the piercer washing port
54 washing liquid supply port
62 controller
64 piercer outside surface washer
66 piercer outside surface dryer
68 piercer inside surface washer
70 piercer inside surface dryer
72 washing sequence setter
74 washing sequence holding part

What is claimed:

1. A sampling device comprising:
a probe disposed in a perpendicular orientation so as to aspirate and expel a liquid;
a piercer serving as a cylindrical member inside which the probe can pass, the tip thereof having a pointed end shape so that a cap sealing the upper surface of a sample container inside which a sample is housed is perforated by the tip;
a probe driving mechanism for driving the probe in the horizontal plane direction and in the vertical direction;
a piercer driving mechanism for driving the piercer in the horizontal plane direction and in the vertical direction;
a piercer washing port provided at a position to which the piercer can move, the position differing from the position at which the piercer executes the perforation operation of the cap on the upper surface of the sample container, the piercer washing port having an opening in the upper surface and a washing space for washing the piercer inserted from the opening, and a washing liquid discharge channel for discharging the washing liquid being connected beneath the washing space;
a washing liquid expelling mechanism provided on the piercer washing port so as to simultaneously expel the washing liquid from a plurality of washing liquid expelling ports disposed at equal spaces on the periphery along the inside wall surface of the washing space to the piercer inserted into the washing space; and
a controller for controlling the operations of the probe driving mechanism, the piercer driving mechanism, and the washing liquid expelling mechanism, the controller being equipped with a piercer outside surface washer for executing a piercer outside surface washing operation to expel the washing liquid from the washing liquid discharge mechanism in a state in which the piercer is disposed inside the washing space,
wherein the piercer outside surface washing operation is performed by moving the piercer in the vertical direction while forming a film consisting of the washing liquid in the circumferential direction on the outer peripheral surface of the piercer so that the film formation range covers the washing range of the outer peripheral surface of the piercer.

2. The sampling device according to claim 1, wherein the washing liquid expelling mechanism is configured to expel a washing liquid diagonally downward from the washing liquid expelling port.

3. A sampling device comprising:
a probe disposed in a perpendicular orientation so as to aspirate and expel a liquid;
a piercer serving as a cylindrical member inside which the probe can pass, the tip thereof having a pointed end shape so that a cap sealing the upper surface of a sample container inside which a sample is housed is perforated by the tip;
a probe driving mechanism for driving the probe in the horizontal plane direction and in the vertical direction;
a piercer driving mechanism for driving the piercer in the horizontal plane direction and in the vertical direction;
a piercer washing port provided at a position to which the piercer can move, the position differing from the position at which the piercer executes the perforation operation of the cap on the upper surface of the sample container, the piercer washing port having an opening in the upper surface and a washing space for washing the piercer inserted from the opening, and a washing liquid discharge channel for discharging the washing liquid being connected beneath the washing space;

a washing liquid expelling mechanism provided on the piercer washing port so as to simultaneously expel the washing liquid from a plurality of washing liquid expelling ports disposed at equal spaces on the periphery along the inside wall surface of the washing space to the piercer inserted into the washing space; and a controller for controlling the operations of the probe driving mechanism, the piercer driving mechanism, and the washing liquid expelling mechanism, the controller being equipped with a piercer outside surface washer for executing a piercer outside surface washing operation to expel the washing liquid from the washing liquid discharge mechanism in a state in which the piercer is disposed inside the washing space, wherein the piercer washing port is further equipped with an air injection mechanism for blowing air onto the piercer housed in the washing space from the periphery thereof; and the controller is further equipped with a piercer outside surface dryer for executing a piercer outside surface drying operation of blowing air onto the piercer from the air injection mechanism.

4. The sampling device according to claim 3 wherein the air injection mechanism is configured so as to blow air onto the piercer in a diagonally downward direction.

5. A sampling device comprising:
a probe disposed in a perpendicular orientation so as to aspirate and discharge a liquid;
a piercer serving as a cylindrical member inside which the probe can pass, the tip thereof having a pointed end shape so that a cap sealing the upper surface of a sample container inside which a sample is housed is perforated by the tip;
a probe driving mechanism for driving the probe in the horizontal plane direction and in the vertical direction;
a piercer driving mechanism provided as a separate mechanism from the probe driving mechanism so as to drive the piercer in the horizontal plane direction and in the vertical direction;
a piercer washing nozzle positioned above the piercer so as to be able to expel a washing liquid into the piercer;
a washing liquid discharge port for discharging the washing liquid expelled from the piercer washing nozzle; and
a controller for controlling the operations of the probe driving mechanism, the piercer driving mechanism, and the piercer washing nozzle, the controller having a piercer inside surface washer for executing a piercer inside surface washing operation to expel the washing liquid from the piercer washing nozzle toward the inside of the piercer in a state in which the piercer is disposed inside the washing liquid discharge port and the piercer washing nozzle is disposed above the piercer.

6. The sampling device according to claim 5, wherein the device is further equipped with a washing port provided at a position to which the piercer can move, the position differing from the position at which the piercer executes the perforation operation of the cap on the upper surface of the sample container;
the washing port has an opening in the upper surface and a washing space for washing the piercer inserted from the opening, and a washing liquid discharge channel for discharging the washing liquid is connected beneath the washing space so as to serve as the washing liquid discharge port;

a washing liquid expelling mechanism is provided on the piercer washing port so as to simultaneously expel the washing liquid from a plurality of washing liquid expelling ports disposed at equal spaces on the periphery along the inside wall surface of the washing space to the piercer inserted into the washing space and to thereby form a film consisting of the washing liquid in the circumferential direction on the outer peripheral surface of the piercer; and the controller is further equipped with a piercer outside surface washer for executing a piercer outside surface washing operation to expel the washing liquid from the washing liquid discharge mechanism in a state in which the piercer is disposed inside the washing space.

7. The sampling device according to claim 6, wherein the piercer outside surface washing operation is performed by moving the piercer in the vertical direction while forming a film consisting of the washing liquid in the circumferential direction on the outer peripheral surface of the piercer so that the film formation range covers the washing range of the outer peripheral surface of the piercer.

8. The sampling device according to claim 6, wherein the washing liquid expelling mechanism is configured to expel a washing liquid diagonally downward from the washing liquid expelling port.

9. A sampling device comprising:
a probe disposed in a perpendicular orientation so as to aspirate and discharge a liquid;
a piercer serving as a cylindrical member inside which the probe can pass, the tip thereof having a pointed end shape so that a cap sealing the upper surface of a sample container inside which a sample is housed is perforated by the tip;
a probe driving mechanism for driving the probe in the horizontal plane direction and in the vertical direction;
a piercer driving mechanism provided as a seperate mechanism from the probe driving mechanism so as to drive the piercer in the horizontal plane direction and in the vertical direction;
a piercer washing nozzle positioned above the piercer so as to be able to expel a washing liquid into the piercer;
a washing liquid discharge port for discharging the washing liquid expelled from the piercer washing nozzle; and
a controller for controlling the operations of the probe driving mechanism, the piercer driving mechanism, and the piercer washing nozzle, the controller having a piercer inside surface washer for executing a piercer inside surface washing operation to expel the washing liquid from the piercer washing nozzle toward the inside of the piercer in a state in which the piercer is disposed inside the washing liquid discharge port and the piercer washing nozzle is disposed above the piercer, wherein the piercer washing nozzle is able to inject air at a timing differing from that of the washing liquid; and
the controller is further equipped with a piercer inside surface dryer for executing a piercer inside surface drying operation of injecting air from the piercer washing nozzle in a state in which the piercer is disposed inside the washing liquid discharge port and the piercer washing nozzle is disposed above the piercer.

10. A sampling device comprising:
a probe disposed in a perpendicular orientation so as to aspirate and discharge a liquid;
a piercer serving as a cylindrical member inside which the probe can pass, the tip thereof having a pointed end shape so that a cap sealing the upper surface of a sample container inside which a sample is housed is perforated by the tip;

a probe driving mechanism for driving the probe in the horizontal plane direction and in the vertical direction;

a piercer driving mechanism provided as a separate mechanism from the probe driving mechanism so as to drive the piercer in the horizontal plane direction and in the vertical direction;

a piercer washing nozzle positioned above the piercer so as to be able to expel a washing liquid into the piercer;

a washing liquid discharge port for discharging the washing liquid expelled from the piercer washing nozzle; and a controller for controlling the operations of the probe driving mechanism, the piercer driving mechanism, and the piercer washing nozzle, the controller having a piercer inside surface washer for executing a piercer inside surface washing operation to expel the washing liquid from the piercer washing nozzle toward the inside of the piercer in a state in which the piercer is disposed inside the washing liquid discharge port and the piercer washing nozzle is disposed above the piercer wherein the device is further equipped with a washing port provided at a position to which the piercer can move, the position differing from the position at which the piercer executes the perforation operation of the cap on the upper surface of the sample container;

the washing port has an opening in the upper surface and a washing space for washing the piercer inserted from the opening, and a washing liquid discharge channel for discharging the washing liquid is connected beneath the washing space so as to serve as the washing liquid discharge port;

a washing liquid expelling mechanism is provided on the piercer washing port so as to simultaneously expel the washing liquid from a plurality of washing liquid expelling ports disposed at equal spaces on the periphery along the inside wall surface of the washing space to the piercer inserted into the washing space and to thereby form a film consisting of the washing liquid in the circumferential direction on the outer peripheral surface of the piercer, and the controller is further equipped with a piercer outside surface washer for executing a piercer outside surface washing operation to expel the washing liquid from the washing liquid discharge mechanism in a state in which the piercer is disposed inside the washing space, wherein the piercer washing port is further equipped with an air injection mechanism for blowing air onto the piercer housed in the washing space from the periphery thereof; and the controller is further equipped with a piercer outside surface dryer for executing a piercer outside surface drying operation of blowing air onto the piercer from the air injection mechanism in a state in which the piercer is disposed inside the washing liquid discharge port and the piercer washing nozzle is disposed above the piercer.

11. The sampling device according to claim 10, wherein the air injection mechanism is configured so as to blow air onto the piercer in a diagonally downward direction.

12. The sampling device according to claim 10, wherein the device is further equipped with a washing sequence holding part for holding the timing at which each of the operations including piercer inside surface washing operation, the piercer outside surface washing operation, the piercer inside surface drying operation, and the piercer outside surface drying operation when the washing of the piercer is executed; and the washing sequence holding part holds a washing sequence configured so that the piercer inside surface drying operation is executed after executing the piercer inside surface washing operation and the piercer outside surface washing operation and so that the piercer outside surface drying operation is executed during the execution of the piercer inside surface drying operation.

\* \* \* \* \*